United States Patent [19]

Martin et al.

[11] Patent Number: 4,738,357
[45] Date of Patent: Apr. 19, 1988

[54] ELEMENT FOR RECEIVING A CONDOM

[76] Inventors: Claus Martin, Liechtensteinstr. 22, 7408 Wankheim; Jan Hulik, Beim Herbstenhof 38, 7400 Tübingen, both of Fed. Rep. of Germany

[21] Appl. No.: 34,728

[22] Filed: Apr. 6, 1987

[30] Foreign Application Priority Data

Feb. 27, 1987 [DE] Fed. Rep. of Germany ....... 3706313

[51] Int. Cl.⁴ ................................................ A61F 5/44
[52] U.S. Cl. ..................................... 206/69; 206/400; 206/408; 604/349
[58] Field of Search ............................... 206/398–402, 206/408, 303, 69; 604/349, 353, 352

[56] References Cited

U.S. PATENT DOCUMENTS

| | | | |
|---|---|---|---|
| 713,964 | 11/1902 | Clark | 206/303 |
| 1,573,484 | 2/1926 | Franklin | 206/303 |
| 3,536,192 | 10/1970 | Couper | 206/303 |
| 3,737,028 | 6/1973 | Carlson | 206/400 |
| 3,746,159 | 7/1973 | May | 206/303 |

Primary Examiner—Joseph Man-Fu Moy
Attorney, Agent, or Firm—Bachman & LaPointe

[57] ABSTRACT

An element for receiving a condom is proposed, which receives the roll of rolled up condom in an annular hollow profile. The front end of the condom projects out of an annular clearance and is protected against unintentional damage by means of two protective disks. The element greatly facilitates handling and requires no additional packing.

11 Claims, 1 Drawing Sheet

U.S. Patent
Apr. 19, 1988
4,738,357
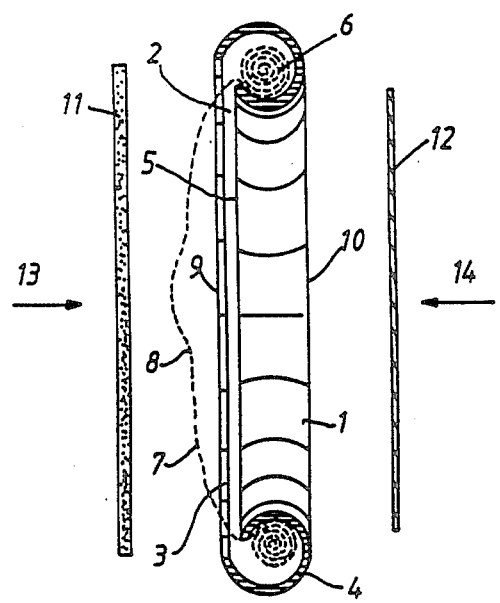
FIG.1
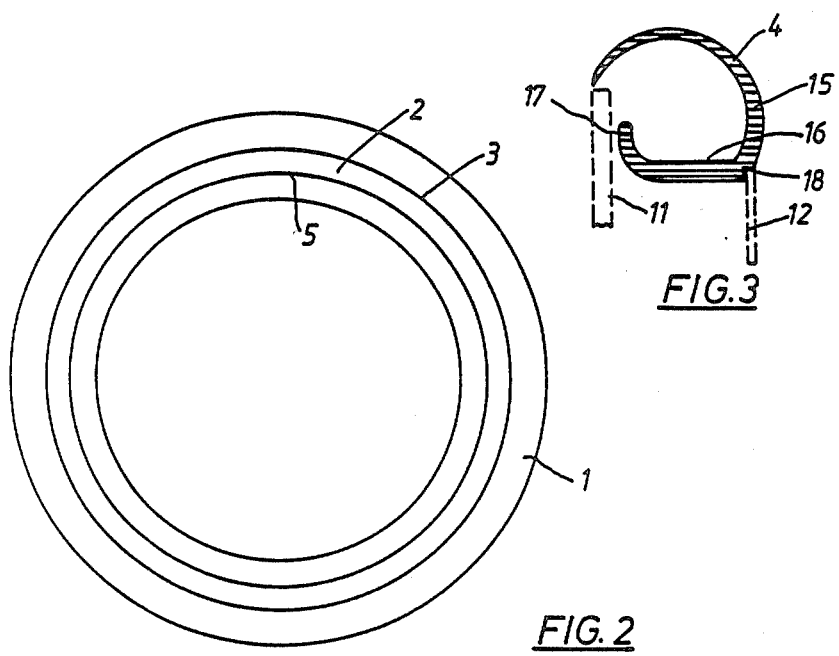
FIG.2
FIG.3

ELEMENT FOR RECEIVING A CONDOM

The invention relates to an element for receiving a condom.

Condoms which are used for contraceptive purposes and for providing protection against infectious diseases are normally packaged in a rolled up state in thin-walled plastic envelopes. On tearing open said plastic envelopes, there is a risk of damaging the condom. It is also difficult to handle condoms, because it must always be taken into account that the condom can only be unrolled in one direction.

The problem of the present invention is to provide an element for receiving a rolled up condom, which facilitates the handling of the latter.

This problem is solved by the features given in the main claim. The rolled up condom is securely stored in an annular hollow profile, the front end of the condom projecting out of an annular clearance. Thus, for using the condom, it is merely necessary to engage over the penis the annular element with the condom, the condom roll unrolling in the hollow profile. When the condom is completely unrolled, the annular element can be removed from the penis in the opposite direction.

The annular element is preferably made from an adequately stable plastic, which surrounds the inserted roll so as to prevent damage. The condom roll is stored with pretension in the inventive element and this is brought about in that the internal diameter of the hollow profile is larger than the internal diameter of the roll. As a result of this mechanical tension resulting from limited expansion, a problem-free unrolling of the roll is ensured at the time of use.

The element is preferably constructed as a ring with a C-shaped hollow profile and the open gap can be made smaller than the roll diameter.

In the vicinity of the annular clearance there can also be a radially directed projection, which prevents the roll from unintentionally slipping off prior to complete unrolling.

The invention is described in greater detail hereinafter relative to the drawings, wherein show:

FIG. 1 An annular element with a condom inserted in the hollow profile in section.

FIG. 2 A view of the annular surface with annular clearance of the element shown in FIG. 1.

FIG. 3 Another embodiment for the hollow profile.

In the case of the annular element 1 shown in FIG. 1, an annular clearance is formed, which is radially outwardly defined by a projection 3 of hollow profile 4. The other boundary of the annular clearance 2 is formed by an edge 5 set back with respect to projection 3.

The substantially C-shaped hollow profile 4 contains the roll 6 of a condom 7, which is here shown by means of broken lines. The front end 8 of condom 7 projects out of the annular clearance 2, whilst roll 6 is elastically fixed in hollow profile 4.

The two end faces 9, 10 are covered with protective disks 11, 12, which are mounted on element 1 in the direction of arrows 13, 14. Protective disk 11 is made from a more stable material, whilst protective disk 12 can be made from a relatively thin film. Protective disks 11, 12 protect the condom 7 against unintentional damage. In addition, protective disk 11 can only be forced outwards from element 1 in the direction of arrow 14. This ensures that element 1 and therefore the condom 7 stored therein can only be engaged over the penis from side 10, accompanied by the unrolling of roll 6 of condom 7. When roll 6 is completely unrolled, element 1 can be removed in the opposite direction. Protective disk 12 is made from such a thin film that it can be pressed in without difficulty.

FIG. 2 shows the end face of element 1 containing annular clearance 2.

FIG. 3 shows another profile 15 for hollow profile 4. Profile 15 has a horizontally directed area 16, which receives the roll 6 of condom 7. A connecting, radially directed edge 17 prevents roll 6 from slipping out prior to complete unrolling. Protective disks 11, 12 are again provided, protective disk 12 engaging in a corresponding set back step 18 on element 1.

In place of a rolled up condom, the condom part stored in the element can be inserted into the hollow profile, so that a fold is formed.

Marks or the like can be made on element 1 for distinguishing the two sides thereof by means of the sense of touch.

We claim:

1. In combination a substantially annular container having a substantially annular hollow profile and a condom inserted therein, said combination characterized in that:
    the condom is in the form of a substantially annular roll and is substantially located within the hollow profile;
    said hollow profile having an annular slot through which a front end of the condom projects; and
    protective disks disposed on opposed sides of the container to cover the front end of the condom.

2. The combination according to claim 1 further characterized by said condom roll being stored within said container in an elastically pretensioned manner.

3. The combination according to claim 1 further characterized in that said container is shaped as a ring having a C-shaped profile.

4. The combination according to claim 1 further characterized by a projection formed on the hollow profile for preventing said condom from slipping out of said container.

5. The combination according to claim 1 further characterized by said slot being narrower than the diameter of said condom roll.

6. The combination according to claim 1 further characterized by said container having an internal diameter of approximately 3.5 cm.

7. The combination according to claim 1 further characterized by one of said protective disks being outwardly pressable only through the free inner area of the annular container.

8. The combination according to claim 7 further characterized in that said outwardly pressable protective disk is made from a stable material and the other of said disks is made from an easily destructable material.

9. The combination according to claim 8 wherein said outwardly pressable protective disk is formed from at least one of cardboard and plastic and said other disk is formed from at least one of paper and a plastic film.

10. The combination according to claim 1 further characterized in that said condom stored within said hollow profile is inserted into said hollow profile in folds.

11. The combination according to claim 1 further characterized in that an external portion of said container has at least one of marks and projections for permitting the sides of said structure to be distinguished by the sense of touch.

* * * * *